US00PP19146P2

(12) United States Plant Patent
Kleinhanns

(10) Patent No.: US PP19,146 P2
(45) Date of Patent: Aug. 26, 2008

(54) ***PETUNIA* PLANT NAMED 'GLOW LAVENDER SHADES'**

(50) Latin Name: *Petunia hybrida*
Varietal Denomination: Glow Lavender Shades

(75) Inventor: Christoph E. Kleinhanns, Gernrode (DE)

(73) Assignee: Hamer Bloemzaden B.V., H.I. Ambacht (NL)

( * ) Notice: Subject to any disclaimer, the term of this patent is extended or adjusted under 35 U.S.C. 154(b) by 0 days.

(21) Appl. No.: 11/827,215

(22) Filed: Jul. 11, 2007

(51) Int. Cl.
*A01H 5/00* (2006.01)

(52) U.S. Cl. ..... Plt./356
(58) Field of Classification Search ..... Plt./356
See application file for complete search history.

*Primary Examiner*—Wendy C. Haas
(74) *Attorney, Agent, or Firm*—Jondle & Associates, P.C.

(57) ABSTRACT

A *petunia* cultivar particularly distinguished by light to dark violet flowers, early flowering and a compact plant habit is disclosed.

1 Drawing Sheet

Genus and species: *Petunia hybrida.*
Variety denomination: 'Glow Lavender Shades'.

BACKGROUND OF THE NEW PLANT

The present invention comprises a new and distinct cultivar of *petunia,* botanically known as *Petunia hybrida,* and hereinafter referred to by the cultivar name 'Glow Lavender Shades'. 'Glow Lavender Shades' originated from a hybridization in May 2002 in Quedlinburg, Germany. The female parent was a *petunia* with light purple flowers while the male parent was a *petunia* with light rose-purple flowers.

The new cultivar was first propagated in Summer of 2006 from mother stock and has been asexually reproduced through vegetative cuttings for five generations. present invention has been found to retain its distinctive characteristics through successive asexual propagations.

SUMMARY OF THE INVENTION

The following are the most outstanding and distinguishing characteristics of this new cultivar when grown under normal horticultural practices in Quedlinburg, Germany.

1. Light to dark violet flowers;
2. Early flowering; and
3. Compact plant habit.

DESCRIPTION OF THE PHOTOGRAPH

This new *petunia* plant is illustrated by the accompanying photograph which shows the overall plant habit, including blooms, buds and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Glow Lavender Shades'. The data which defines these characteristics were collected from asexual reproductions carried out in Quedlinburg, Sachsen-Anhalt, Germany. Data was collected on plants in 12 inch pots in October. Color references are primarily to the R.H.S.

Colour Chart of The Royal Horticultural Society of London (R.H.S.) (4$^{th}$ ed). Anatomic labels are from The Cambridge Illustrated Glossary of Botanical Terms, by M. Hickey and C. King, Cambridge University Press.

DETAILED BOTANICAL DESCRIPTION

Classification:
- *Family.*—Solanaceae.
- *Botanical.*—*Petunia hybrida.*
- *Common name.*—*Petunia.*

Parengate:
- *Female parent.*—*Petunia* with light purple flowers.
- *Male parent.*—*Petunia* with light rose-purple flowers.

Plant:
- *Form.*—Trailing.
- *Habit.*—Upright, later trailing.
- *Height.*—15.0 cm to 35.0 cm.
- *Width.*—Radius: 20.0 cm to 45.0 cm. Diameter: 40.0 cm to 90.0 cm.
- *Propagation.*—Terminal tip cuttings.
- *Time to produce a finished flowering plant.*—10 to 12 weeks.
- *Time to initiate and develop roots.*—4 to 5 weeks.
- *Root description.*—Fine rooting system, with white to light brown roots.

Stems:
- *Average number.*—5 to 20.
- *Length of basal branches.*—50.0 cm to 80.0 cm.
- *Internode length.*—1.0 cm to 6.0 cm.
- *Diameter of branches.*—Radius: Less than 0.1 cm to 0.3 cm. Diameter: 0.1 cm to 0.6 cm.
- *Stem color.*—RHS 141A (Dark-green).
- *Anthocyanin.*—Absent.
- *Texture.*—Pubescent.

Leaves:
- *Arrangement.*—Alternate.
- *Size.*—Length: 2.0 cm to 4.0 cm. Width: 0.5 cm to 2.5 cm.
- *Shape.*—Oval to ovate, sometimes running spiky to the apex.
- *Margin.*—Entire.

*Apex.*—Spiky.

*Base.*—Round running to the stem.

*Immature leaf.*—General color: RHS 135A (Dark green). Upper surface: RHS 141A (Dark green). Lower surface: RHS 141C (Lighter green). Texture: Pubescent.

*Mature leaf.*—General color: RHS 131A (Light green). Upper surface: RHS 141A (Dark green). Lower surface: RHS 141C (Lighter green).

*Texture.*—Pubescent, mucilaginous.

*Venation.*—Indistinct.

*Petioles.*—Leaves nearly distinct on the branches.

Flower bud:

*Shape.*—Long tube.

*Size.*—Length: 3.5 cm to 5.0 cm. Diameter: Radius: 0.1 cm to 0.3 cm. Diameter: 0.2 cm to 0.6 cm.

*Immature flower color.*—RHS 92A (Violet) to RHS 93B (Purple).

Inflorescence:

*Blooming habit* (*flowering season*).—May to November.

*Inflorescence type.*—Single flowers.

*Number of flowers per node.*—1.

*Lastingness of individual blooms on the plant.*—About 7 days, but very much dependent on irrigation, fertilizer and temperature.

*Fragrance.*—Soft.

*Pedicels.*—Color: RHS 139A (Dark-green). Length: 1.0 cm to 5.0 cm. Diameter: Radius: Less than 0.1 cm to 0.1 cm. Diameter: 0.1 cm to 0.2 cm. Texture: Pubescent.

Flowers:

*Shape.*—Funnel shaped.

*Size.*—Diameter: Radius: 2.5 cm to 4.0 cm. Diameter: 5.0 cm to 8.0 cm. Depth: 4.0 cm to 6.0 cm. Funnel: Length: 2.5 cm to 3.5 cm. Diameter: Radius: 0.3 cm to 0.6 cm. Diameter: 0.6 cm to 1.2 cm. Outside texture: Pubescent. Outside color: RHS 92A (violet) with RHS 139C (Green).

*Mature flower.*—Face/Margin Color: RHS 94C to RHS 88A (Differs from light to dark violet). Upper surface: RHS 91A to RHS 91B (Violet). Lower surface: RHS 91B to RHS 91C (Lighter violet). Corolla tube: Shape of corolla: Open funnel shaped. Color inside (throat): RHS 90A (Dark violet veined with some green). Color outside: RHS 90A (Dark violet veined with some green). Petals: Apex: Nearly round. Base: Fused. Margin: Entire. Waviness: Very soft. Location: Moderate lobing. Texture: Glabrous.

*Calyx arrangement.*—Symmetric.

*Sepals.*—Number: 5. Color: RHS 139B (Green). Length: 1.0 cm to 2.0 cm. Width: 0.2 cm to 0.5 cm. Shape: Not fused, long. Apex: Nearly round. Base: Long. Margin: Entire. Texture: Pubescent.

Reproductive organs:

*Stamens.*—Quantity: 5. Shape: Cylindrical. Color: RHS 139D (Light-green). Filament length: 0.8 cm to 1.8 cm. Filament diameter: Radius: Less than 0.1 cm. Diameter: Less than 0.1 cm.

*Anther.*—Shape: Oval. Color: RHS 4D (Cream-yellow). Length: 0.2 cm to 0.4 cm. Diameter: Radius: 0.1 cm to 0.15 cm. Diameter: 0.2 cm to 0.3 cm.

*Pollen.*—Color: RHS 4C (Light yellow). Amount: Abundant.

*Pistils.*—Number: 1. Length: 2.0 cm to 3.0 cm. Diameter: Radius: Less than 0.1 cm. Diameter: 0.1 cm. Stigma: Color: RHS 139D (Light green). Shape: Oval. Length: 0.1 cm to 0.2 cm. Diameter: Radius: 0.1 cm to 0.15 cm. Diameter: 0.2 cm to 0.3 cm. Style: Color: RHS 139D (Light green). Length: 1.9 cm to 2.8 cm. Diameter: Radius: Less than 0.1 cm. Diameter: Less than 0.1 cm. Shape: Long cylindrical.

Seeds:

*Color.*—RHS 175A (Dark orange-brown).

*Length.*—0.1 cm.

*Diameter.*—Radius: Less than 0.1 cm. Diameter: Less than 0.1 cm. Shape: Round.

Disease and insect resistance: Resistance and susceptibility is typical of the species.

COMPARISON WITH KNOWN CULTIVARS

'Glow Lavender Shades' differs from the female parent *petunia* plant in that the female parent has a more upright habit than 'Glow Lavender Shades'. Additionally 'Glow Lavender Shades' has a light to dark violet flower color, while the female parent has a light purple flower color.

'Glow Lavender Shades' differs from the male parent *petunia* plant in that the male parent has a more trailing growth habit than 'Glow Lavender Shades'. Additionally, 'Glow Lavender Shades' has a light to dark violet flower color, while the male parent has a very light rose-purple flower color.

'Glow Lavender Shades' differs from commercial *petunia* variety 'Red Fox SURPRISE Lavender' (U.S. Plant Patent applied for) in that 'Glow Lavender Shades' has a more upright growth habit than 'Red Fox SURPRISE Lavender'. Additionally, 'Glow Lavender Shades' has a flower color of RHS 91A to RHS 91B, while 'Red Fox SURPRISE Lavender' has a flower color of RHS 91D.

I claim:

1. A new and distinct cultivar of *petunia* plant as described and shown herein.

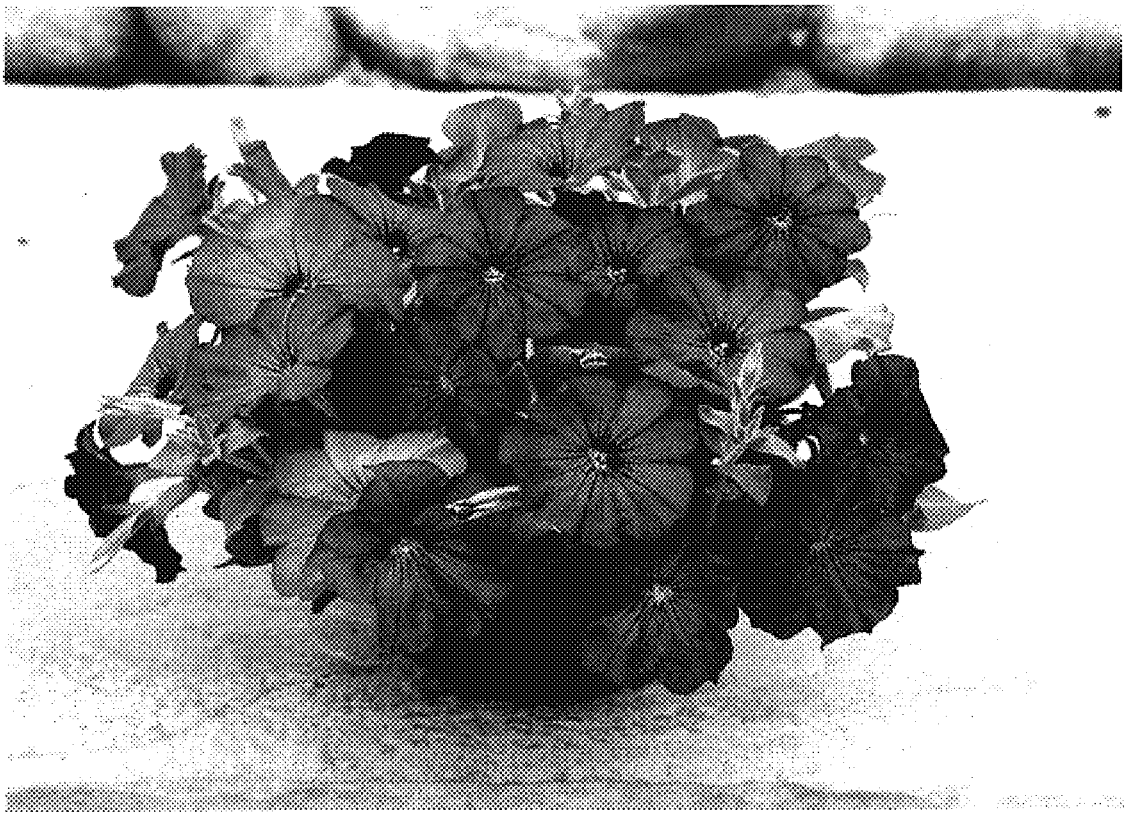

* * * * *